(12) United States Patent
Candau et al.

(10) Patent No.: US 7,959,903 B2
(45) Date of Patent: Jun. 14, 2011

(54) OIL-IN-WATER PHOTOPROTECTIVE EMULSIONS CONTAINING GEMINI SURFACTANTS AND ASSOCIATIVE POLYMERS

(75) Inventors: Didier Candau, Bievres (FR); Christele Gombert, La Morlaye (FR)

(73) Assignee: L'Oreal, Paris (FR)

( * ) Notice: Subject to any disclaimer, the term of this patent is extended or adjusted under 35 U.S.C. 154(b) by 1891 days.

(21) Appl. No.: 10/902,373

(22) Filed: Jul. 30, 2004

(65) Prior Publication Data

US 2005/0063925 A1    Mar. 24, 2005

Related U.S. Application Data

(60) Provisional application No. 60/515,642, filed on Oct. 31, 2003.

(30) Foreign Application Priority Data

Aug. 1, 2003  (FR) .................... 03 09540

(51) Int. Cl.
*A61K 8/00* (2006.01)
*A61K 31/74* (2006.01)
*C11D 1/755* (2006.01)

(52) U.S. Cl. ........ 424/59; 424/78.03; 424/486; 510/493

(58) Field of Classification Search .................... 424/59, 424/78.03, 486; 510/493
See application file for complete search history.

(56) References Cited

U.S. PATENT DOCUMENTS

| | | | | |
|---|---|---|---|---|
| 5,952,290 A | * | 9/1999 | Li et al. | 510/493 |
| 6,409,998 B1 | * | 6/2002 | Candau et al. | 424/59 |
| 6,630,133 B1 | | 10/2003 | Dupuis | |
| 6,710,022 B1 | * | 3/2004 | Kwetkat et al. | 510/119 |
| 2003/0124079 A1 | | 7/2003 | Mougin et al. | |

FOREIGN PATENT DOCUMENTS

| | | |
|---|---|---|
| EP | 1 084 695 A1 | 3/2001 |
| EP | 1 093 796 A1 | 4/2001 |
| EP | 1 174 450 A1 | 1/2002 |
| JP | 11-060437 * | 3/1999 |
| WO | WO 0119945 A1 * | 3/2001 |
| WO | 03/024412 A2 | 3/2003 |

* cited by examiner

*Primary Examiner* — Johann R Richter
*Assistant Examiner* — Andriae M Holt
(74) *Attorney, Agent, or Firm* — Buchanan Ingersoll & Rooney, P.C.

(57) ABSTRACT

The invention relates to a photoprotective composition containing as liquid phase, an oil-in-water emulsion, emulsified with at least one dimeric surfactant comprising two surfactant units, which may be identical or different, each consisting of a hydrophilic head and a hydrophobic tail and connected to each other, via the hydrophilic heads, by means of a spacer group, at least one photoprotective system capable of screening out UV rays, containing at least one mineral nanopigment based on metal oxide, and optionally at least one organic, preferably hydrosoluble or liposoluble UV-A and/or UV-B screening agent, and at least one associative polymer comprising at least one $C_{8-40}$ fatty chain, and also to a process for preparing such a photoprotective composition.

22 Claims, No Drawings

OIL-IN-WATER PHOTOPROTECTIVE EMULSIONS CONTAINING GEMINI SURFACTANTS AND ASSOCIATIVE POLYMERS

This application claims the priority of U.S. Provisional Application No. 60/515,642, filed Oct. 31, 2003, incorporated by reference herein in its entirety and relied upon.

The present invention relates to photoprotective compositions for protecting the skin and/or the hair against UV radiation, containing nanopigments based on metal oxides in an oil-in-water liquid phase emulsified with a gemini surfactant in the presence of an associative polymer, and also to a process for preparing such compositions.

Many cosmetic compositions for photoprotecting the skin have been proposed to date. These compositions generally contain, in an emulsified liquid support (oil-in-water emulsion), one or more organic molecules capable of absorbing ultraviolet radiation, which are soluble in the oily and/or aqueous phase. The use of mineral nanopigments in such antisun compositions is increasingly common since these particles, which are invisible to the naked eye by virtue of their small size, make it possible to increase the protection factor of the compositions containing them.

Among these known antisun products, fluid oil-in-water emulsions are generally more appreciated by consumers than thicker emulsions, since they have a more pleasant feel and allow the product to be applied more easily.

One of the major drawbacks of these fluid antisun compositions containing mineral nanopigments lies in the difficulty of finding a compromise between good stability of the product and effective protection. Specifically, to obtain emulsions of low viscosity, i.e. emulsions in which the droplets of the dispersed phase are very small, it is generally necessary to use extremely powerful stirring means such as high-pressure homogenizers. The manufacture of fluid emulsions with such equipment is very expensive and does not allow the introduction of nanopigments during the emulsification phase. The reason for this is that the particles can clog up the fine nozzles of these machines and can, when, like titanium dioxide, they are of high hardness, have a highly abrasive effect resulting in deterioration of the homogenizer.

One approach for overcoming this problem consists in incorporating the nanopigments not before or during the emulsification step, but after the said step. To do this, it has been proposed to mix concentrated emulsions containing only a portion of the final aqueous phase, with an aqueous dispersion of the nanopigment. These aqueous dispersions must be stabilized with dispersants, and relatively large amounts of molecules with surface activity, which are liable to disrupt the surfactant film at the oil/water interface, are thus introduced into the emulsion. The stability of such emulsions is generally limited over time and the final product then no longer has the organoleptic qualities and protection efficacy that are essential for its commercialization.

Another possibility consists in incorporating the nanopigments not in the form of an aqueous dispersion, but in pulverulent form. The drawback of this method lies in the fact that the more fluid the emulsion, the more difficult it will be to obtain a homogeneous and stable dispersion of the nanoparticles. The pigment poorly dispersed in the final product is then in the form of aggregates, which, when applied to the skin, give it a whitish appearance that is cosmetically undesirable and scarcely appreciated by users. This effect is all the more pronounced the higher the concentration of nanopigments in the emulsion. Poor distribution of the nanopigments at the surface of the skin is furthermore responsible for the poor efficacy of the product.

There is thus still a need for a process for preparing photoprotective emulsions containing nanopigments, which makes it possible, by simple mixing of the various components, i.e. of the emulsified liquid phase and of the nanopigments, to obtain relatively fluid compositions that are easy and pleasant to apply, giving effective sun protection and having good stability over time.

The Applicant has found, surprisingly, that the combined use of at least one surfactant chosen from a particular family of surfactants described in greater detail hereinbelow, and of at least one associative polymer makes it possible to prepare emulsified fluid antisun compositions containing nanopigments, without the need for high-pressure emulsification techniques.

According to the invention, the term "fluid" compositions means compositions with a viscosity, measured at 25° C. using a Brookfield viscometer with a No. 7 needle, of less than 200 mPa·s and preferably between 10 and 180 mPa·s.

The surfactants participating in solving the problem of the present invention are dimeric surfactants, usually referred to as gemini surfactants, comprising two surfactant units each consisting of a hydrophilic head and a hydrophobic tail and connected to each other, via the hydrophilic heads, by means of a spacer group.

Associative polymers are water-soluble polymers that are capable, in an aqueous medium, of reversibly combining with each other or with other molecules.

Their chemicals structure comprises hydrophilic zones, which give them their solubility in water, and hydrophobic zones comprising a fatty chain, allowing them to associate via hydrophobic interaction with each other or with other molecules comprising hydrophobic zones.

One subject of the present invention is consequently a photoprotective composition containing
- as liquid phase, an oil-in-water emulsion, emulsified with at least one dimeric surfactant comprising two surfactant units, which may be identical or different, each consisting of a hydrophilic head and a hydrophobic tail and connected to each other, via the hydrophilic heads, by means of a spacer group,
- a photoprotective system capable of screening out UV rays, containing at least one mineral nanopigment based on metal oxide, and
- at least one associative polymer comprising at least one $C_{8-40}$ fatty chain.

According to one preferred embodiment of the photoprotective compositions of the present invention, the photoprotective system capable of screening out UV rays also contains at least one organic UV-A and/or UV-B screening agent.

The dimeric surfactants or gemini surfactants used in the present invention are known. For a detailed description of the various chemical structures and their physicochemical properties, reference may be made to the following publications:

Milton J. Rosen, Gemini Surfactants, Properties of surfactant molecules with two hydrophilic groups and two hydrophobic groups, Cosmetics & Toiletries magazine, vol. 113, December 1998, pp. 49-55, Milton J. Rosen, Recent Developments in Gemini Surfactants, Allured's Cosmetics & Toiletries magazine, July 2001, vol. 116, No. 7, pp. 67-70.

As preferred examples of gemini surfactants that may be used in the present invention, mention may be made of those collated in German patent application DE 199 43 681 A1, i.e. the compounds of formula (I), described in WO 96/14926:

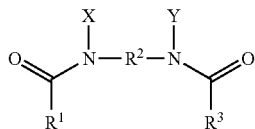

in which
- $R^1$ and $R^3$ represent a linear or branched $C_{5-25}$ alkyl group, which is saturated or containing up to two non-vicinal unsaturations,
- $R^2$ represents a $C_{1-12}$ alkylene group,
- X and Y each represent a group $(C_2H_4O)_x(C_3H_6O)_y$—RF with x=0-15, y=0-10, x+y≧1, and RF=—$SO_3M$, —$CH_2$—$CO_2M$, —P(O)(OM)$_2$, H, —$C_3H_6SO_3M$ or a —$CH_2(CHOH)_4CH_2OH$ group when x+y=0, and
- M represents an alkali metal ion, (alkyl)ammonium, alkanolammonium, H or a ½ alkaline-earth metal ion, of formula (II), described in WO 96/25388:

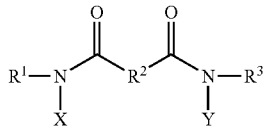

in which the symbols have the same meaning as for formula (I), of formula (III), described in WO 97/31890:

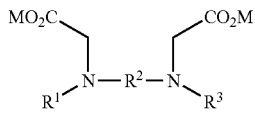

in which the symbols have the meaning indicated for formula (I), of formula (IV), described in DE 196 22 612 and JP-A 10-175 934:

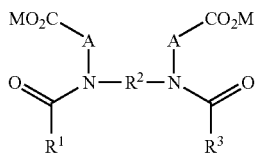

in which
- $R^1$ and $R^3$ represent a linear or branched $C_{5-25}$ alkyl group, which is saturated or containing up to two non-vicinal unsaturations,
- $R^2$ represents a $C_{1-12}$ alkylene group,
- A represents a group —$CHR^4$—, —$CH_2$—, —$C_2H_4$—, —$C_3H_6$— or —$C_4H_8$—,
- $R^4$ represents an aminocarboxylic acid residue, and
- M represents an alkali metal ion, (alkyl)ammonium, alkanolammonium, H or a ½ alkaline-earth metal ion, of formula (V), described in EP 0 708 079:

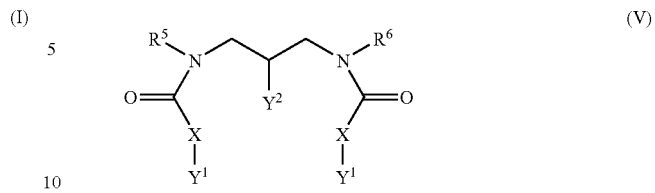

in which
- $R^5$ and $R^6$ represent a linear or branched $C_{6-36}$ alkyl group, which is saturated or containing up to two non-vicinal unsaturations,
- X represents an alkylene or alkenylene group containing from 1 to 6 carbon atoms, which can bear a hydroxyl, sulfonic acid or carboxylic acid group,
- each $Y^1$ independently represents a sulfonate, sulfate, carboxyl or hydroxyl group, a sulfuric acid group or —O—$(CO)_x$—COOH, of formula (VI), described in JP-A-8-311 003:

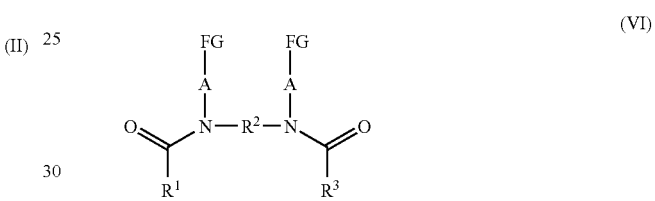

in which the symbols have the meaning given for formula (IV) and FG represents a group —COOM or —$SO_3M$, of formula (VII), described in JP-A-11-60437:

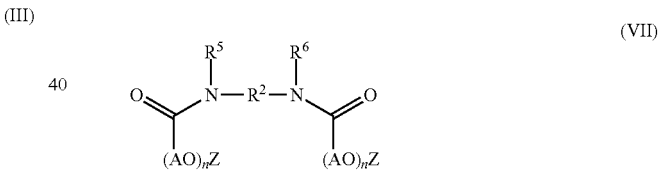

in which the substituents have the meaning indicated for formulae (IV) and (V),
- AO represents an alkyleneoxy unit, for example ethyleneoxy, propyleneoxy and butyleneoxy, n=1 to 20, the alkyleneoxy units possibly being linked together randomly or in blocks, and
- Z represents a group —$SO_3M$, —$C_2H_4SO_3M$, —$C_3H_6SO_3M$, —P(O)(OM)$_2$, —$CH_2$—COOM or —$C_2H_4$—COOM, of formula (VIII), described in EP 0 697 244:

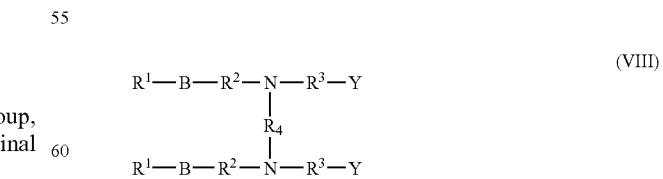

in which
- each $R^1$ represents a linear or branched, optionally hydroxylated or perfluorinated $C_{5-25}$ alkyl group, which is saturated or containing up to two non-vicinal unsaturations, $R^2$ represents an optionally hydroxylated $C_{1-12}$ alkylene group, B represents an amide, carboxyl or polyether group, $R^3$ represents an optionally hydroxylated $C_{1-12}$ alkyl group, a group $R^7$-D-$R^7$ or a polyether group, in which $R^7$ represents an optionally hydroxylated $C_{1-6}$ alkylene group, D represents a group —O—, —S— or —$NR^8$—, $R^4$ represents an optionally hydroxylated alkylene or alkylarylene group comprising from 1 to 12 carbon atoms, or a group $R^9$-$D^1$-$R^9$, $R^8$ represents an optionally hydroxylated $C_{1-12}$ alkyl group, a hydrogen atom or a group $R^9$-$D^1$-$R^9$, $R^9$ represents an optionally hydroxylated $C_{1-6}$ alkylene group or an aryl group, $D^1$=—O—, —S—, —$SO_2$—, —C(O)—, —$O(R^7$—$O)_x$—, $(R^{10})_t[N$—$(R^{10})]$ or an aryl group, $R^{10}$ represents an optionally substituted $C_{1-12}$ alkyl group, a hydrogen atom or an aryl group, t and z are each independently a number between 1 and 4, and each Y independently represents an —$SO_3H$, —$OSO_3H$, —$OP(O)(OH)_2$, —$P(O)(OH)_2$, —COOH or —$CO_2$—$C_6H_4$—$SO_3H$ group and the corresponding salts, of formula (IX), described in EP 0 697 245:

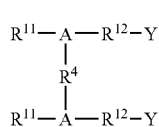

(IX)

in which each $R^{11}$ represents a linear or branched, optionally hydroxylated or perfluorinated $C_{5-12}$ alkyl group, which is saturated or comprising up to two non-vicinal unsaturations, or a group $R^{14}$—B—$R^2$, $R^{14}$ represents a linear or branched, optionally hydroxylated $C_{1-12}$ alkyl group, which is saturated or comprising up to two non-vicinal unsaturations, $R^{12}$ represents a linear or branched, optionally hydroxylated $C_{1-12}$ alkyl group, which is saturated or comprising up to two non-vicinal unsaturations, or an amide, carboxyl, polyether or $R^9$-$D^1$-$R^9$ group, and A represents a group —$CR^2$= or —N=, with the proviso that, when A represents an —N= group, then $R^{11}$ is a group $R^{14}$—B—$R^2$, $R^2$, $R^4$, B, $R^9$ and $D^1$ having the meaning given for formula (VIII), of formula (X), described in DE 42 27 391 and DE 196 08 117:

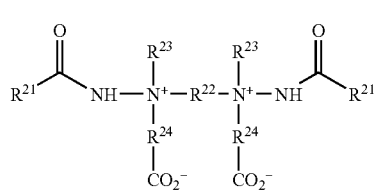

(X)

in which
each $R^{21}$ represents a linear or branched $C_{5-23}$ alkyl group, which is saturated or comprising up to 2 non-vicinal unsaturations, $R^{22}$ and each $R^{24}$ represent a $C_{1-6}$ alkylene group, and each $R^{23}$ represents a methyl, ethyl, propyl or polyether group, of formula (XI), described in U.S. Pat. No. 5,863,886:

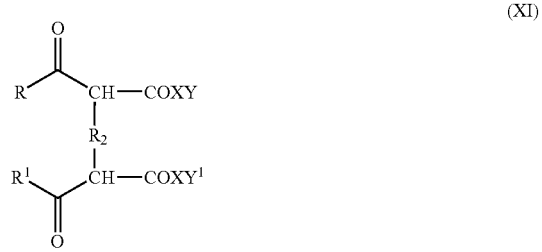

(XI)

in which
R and $R^1$ each represent a linear or branched, optionally hydroxylated or perfluorinated $C_{5-30}$ alkyl group, which is saturated or comprising up to 2 non-vicinal unsaturations, $R^2$ represent an optionally hydroxylated $C_{1-10}$ alkylene or arylene group, a polyether group, —S—, —$SO_2$—, —O—, —S—S—, —O—$R^5$—O— or —S—$R^5$—S—, or a direct bond between the two α carbon atoms, $R^5$ represents a $C_{1-10}$ alkylene, arylene or alkylarylene group, —N($R^6$)— or —($NR^6$)—$R^7$—($NR^6$)—, $R^6$ represents a $C_{1-6}$ alkyl group, $R^7$ represents a $C_{1-6}$ alkylene group, or $R^6$ and $R^7$ form a heterocycle, X represents a polyether group, —O— or —NZ— with Z=H or $C_{1-10}$ alkyl, aryl or alkylaryl, Y and $Y^1$ each independently represent a hydrogen atom or an optionally salified —$CH_2$—COOH group, a carbohydrate residue comprising at least two hydroxyl groups, such as erythrose, threose, ribose, arabinose, xylose, fructose, lyxose, allose, altrose, glucose, mannose or galactose, and mixtures thereof, of formula (XII):

(XII)

in which the symbols have the meaning indicated for formula (XI) and AO represents a group —C(O)—, —C(O)—[—O($R^4$O)$_x$], —$CH_2$—[O($R^4$O)$_x$—)] or —$CH_2$—O, $R^4$ represents a $C_{2-4}$ alkylene group, T and $T^1$ each independently represent a group —OM, —H, —$CH_3$, —$C_2H_5$, —$SO_3M$, —$CH_2COOM$, —$C_2H_4$—COOM, —$C_3H_6$—$CO_3M$, —O—, P(O)(OM)$_2$ and M represents an alkali metal ion or an alkaline-earth metal half-ion, or a mono-, di- or trialkanolammonium ion or a proton, of formula (XIII), described in WO 96/16930:

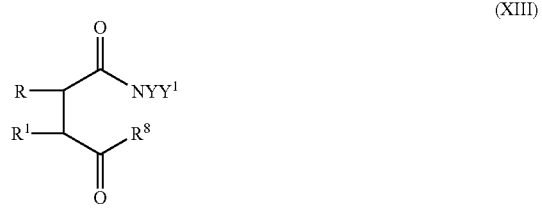

(XIII)

in which the symbols have the meaning indicated for formulae (XI) and (XII) and $R^8$ represents a group $NYY^1$, $—O(R^4O)_xH$ or $—O(R^4O)_x—C(O)—CHR—CHR^1—C(O)NYY^1$, of formula (XIV), described in WO 96/25384:

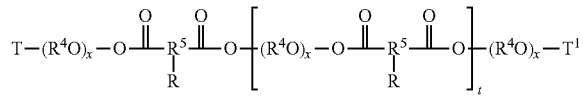

(XIV)

in which the symbols have the meaning indicated for formulae (XI) to (XIII) and t represents an integer ranging from 1 to 100 and preferably from 1 to 4.

Among the above dimeric surfactants that are preferred in particular are anionic surfactants, and in particular those corresponding to formula (I) above. In this family of surfactants, the ones that are preferred in particular are those in which $R^1$ and $R^3$ are identical and each represent a linear $C_{8-16}$ alkyl group, $R^2$ represents a $C_{2-8}$ alkylene group, X and Y each represent a group $—(C_2H_4O)_x—RF$ with x=10-15 and $RF=—SO_3M$, in which M is an alkali metal atom.

One preferred gemini surfactant of this family is an anionic compound of formula:

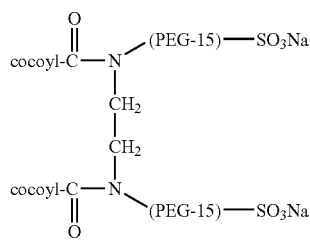

INCI name: sodium dicocoylethylenediamine PEG-15 sulfate.

This gemini surfactant sold by the company Sasol under the name Ceralution® may be used, for example, and especially the following products:

Ceralution® H: Behenyl Alcohol, Glyceryl Stearate, Glyceryl Stearate Citrate and Sodium Dicocoylethylenediamine PEG-15 Sulfate, Ceralution® F: Sodium Lauroyl Lactylate and Sodium Dicocoylethylenediamine PEG-15 Sulfate, Ceralution® C: Aqua, Capric/Caprylic triglyceride, Glycerin, Ceteareth-25, Sodium Dicocoylethylenediamine PEG-15 Sulfate, Sodium Lauroyl Lactylate, Behenyl Alcohol, Glyceryl Stearate, Glyceryl Stearate Citrate, Gum Arabic, Xanthan Gum, Phenoxyethanol, Methylparaben, Ethylparaben, Butylparaben, Isobutylparaben (INCI names).

The concentration of the gemini surfactant(s) used in the present invention is preferably between 0.001% and 8%, preferably between 0.01% and 4% and in particular between 0.05% and 3% relative to the total weight of the photoprotective composition.

The associative polymers used in the present invention may be of anionic, cationic, amphoteric or nonionic type. The associative polymers are preferably nonionic or anionic.

Their weight concentration in the photoprotective composition according to the invention may range from about 0.01% to 10% of the total weight of the composition. This concentration is more preferably between 0.1% and 5% of the total weight of the composition.

Examples of anionic associative polymers that may be mentioned include the following polymers:

(I) polymers comprising at least one hydrophilic unit and at least one fatty-chain allyl ether unit, more particularly those whose hydrophilic unit consists of an ethylenically unsaturated anionic monomer, more particularly still a vinylcarboxylic acid and most particularly an acrylic acid or a methacrylic acid or mixtures thereof, and the hydrophobic unit of which is a $C_{8-30}$ fatty alcohol allyl ether of formula (I) below:

$$CH_2=CR'—CH_2—OB_n—R \quad (I)$$

in which R' denotes H or $CH_3$, B denotes an ethyleneoxy radical, n is zero or denotes an integer ranging from 1 to 100, R denotes a hydrocarbon-based radical chosen from alkyl, arylalkyl, aryl, alkylaryl and cycloalkyl radicals, comprising from 8 to 30 carbon atoms, preferably 10 to 24 carbon atoms and even more particularly from 12 to 18 carbon atoms. A unit of formula (I) that is more particularly preferred is a unit in which R' denotes H, n is equal to 10 and R denotes a stearyl ($C_{18}$) radical.

Anionic associative polymers of this type and their preparation by emulsion polymerization are described in patent application EP-0 216 479.

Among these anionic associative polymers that are particularly preferred are polymers formed from 20% to 60% by weight of acrylic acid and/or of methacrylic acid, from 5% to 60% by weight of lower alkyl (meth)acrylates, from 2% to 50% by weight of fatty-chain allyl ether of formula (I), and from 0% to 1% by weight of a crosslinking agent which is a copolymerizable unsaturated polyethylenic monomer, for instance diallyl phthalate, allyl (meth)acrylate, divinylbenzene, (poly)ethylene glycol dimethacrylate or methylenebisacrylamide.

Among the latter polymers, those most particularly preferred are crosslinked terpolymers of methacrylic acid, of ethyl acrylate and of polyethylene glycol (10 EO) stearyl alcohol ether (Steareth-10), in particular those sold by the company Allied Colloids under the names Salcare SC 80® and Salcare SC 90®, which are aqueous 30% emulsions of a crosslinked terpolymer of methacrylic acid, of ethyl acrylate and of steareth-10 allyl ether (40/50/10).

(II) polymers comprising at least one hydrophilic unit of olefinically unsaturated carboxylic acid type, and at least one hydrophobic unit of unsaturated $C_{10}$-$C_{30}$ alkyl carboxylate type.

Preferably, these polymers are chosen from those in which the hydrophilic unit of unsaturated carboxylic acid type corresponds to the monomer of formula (II):

(II)

in which $R_1$ denotes H, $CH_3$, or $C_2H_5$, that is to say acrylic acid, methacrylic acid or ethacrylic acid units, and in which the hydrophobic unit of unsaturated $C_{10}$-$C_{30}$ alkyl carboxylate type corresponds to the formula (III):

in which $R_2$ denotes H or $CH_3$ or $C_2H_5$ and preferably H or $CH_3$, $R_3$ denoting a $C_{10}$-$C_{30}$ and preferably $C_{12}$-$C_{22}$ alkyl radical.

Unsaturated $C_{10}$-$C_{30}$ alkyl carboxylates according to the invention include, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic associative polymers of this type and their preparation are described in U.S. Pat. Nos. 3,915,921 and 4,509,949.

Among anionic associative polymers of this type that will be used more particularly are polymers synthesized from a monomer mixture essentially comprising acrylic acid, an ester of formula (III) above and in which $R_2$ denotes H or $CH_3$, $R_3$ denotes an alkyl radical containing from 12 to 22 carbon atoms, and a crosslinking agent, which is a copolymerizable polyethylenic unsaturated monomer, for instance diallyl phthalate, allyl (meth)acrylate, divinylbenzene, (poly) ethylene glycol dimethacrylate and methylenebisacrylamide.

Among these anionic associative polymers that will be used more particularly are those consisting of from 95% to 60% by weight of acrylic acid (hydrophilic unit), 4% to 40% by weight of $C_{10}$-$C_{30}$ alkyl acrylate (hydrophobic unit) and 0% to 6% by weight of crosslinking polymerizable monomer, or alternatively those consisting of from 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described above.

Among the said above polymers, those most particularly preferred are the products sold by the company Goodrich under the trade names Pemulen TR1®, Pemulen TR2® and Carbopol 1382®, and even more preferentially Pemulen TR1®, and the product sold by the company SEPPIC under the name Coatex SX®.

(III) maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name Performa V 1608® by the company Newphase Technologies.

(IV) acrylic terpolymers comprising about 20% to 70% by weight of an α,β-unsaturated carboxylic acid, about 20% to 80% by weight of a non-surfactant α,β-unsaturated monomer other than the abovementioned acid, and about 0.5% to 60% by weight of a nonionic surfactant monomer which is the product of reaction of a monohydric surfactant with a monoisocyanate containing ethylenic unsaturation, such as those described in patent application EP-A-0 173 109 and more particularly a methacrylic acid/methyl acrylate/behenyl alcohol dimethyl-meta-isopropenylbenzylisocyanate ethoxylated (40 EO) terpolymer, as an aqueous 25% dispersion, sold under the name Viscophobe DB 1000® by the company Amerchol.

(V) copolymers comprising among their monomers a carboxylic acid containing α,β-monoethylenic unsaturation and an ester of a carboxylic acid containing α,β-monoethylenic unsaturation and of an oxyalkylenated fatty alcohol.

Preferentially, these compounds also comprise as monomer an ester of a carboxylic acid containing α,β-monoethylenic unsaturation and of a $C_1$-$C_4$ alcohol.

An example of a compound of this type that may be mentioned is Aculyn 22® sold by the company Rohm & Haas, which is a methacrylic acid/ethyl acrylate/stearyl methacrylate oxyalkylenated terpolymer.

The cationic associative polymers that may be used in the present invention are, for example:

(I) cationic associative polyurethanes, the family of which has been described by the Applicant in patent application FR 00/09609. These cationic associative polyurethanes may be represented by the general formula (Ia) below:

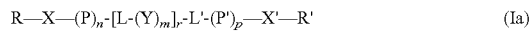

in which:

R and R', which may be identical or different, represent a hydrophobic group or a hydrogen atom;

X and X', which may be identical or different, represent a group comprising an amine function optionally bearing a hydrophobic group, or alternatively a group L";

L, L' and L", which may be identical or different, represent a group derived from a diisocyanate;

P and P', which may be identical or different, represent a group comprising an amine function optionally bearing a hydrophobic group;

Y represents a hydrophilic group;

r is an integer between 1 and 100, preferably between 1 and 50 and in particular between 1 and 25;

n, m and p each range, independently of each other, from 0 to 1000;

the molecule containing at least one protonated or quaternized amine function and at least one hydrophobic group.

In one preferred embodiment of these polyurethanes, the only hydrophobic groups are the groups R and R' at the chain ends.

One preferred family of cationic associative polyurethanes is the one corresponding to formula (Ia) described above and in which R and R' both independently represent a hydrophobic group, X and X' each represent a group L", n and p are between 1 and 1000, and L, L', L", P, P', Y and m have the meaning given above.

Another preferred family of cationic associative polyurethanes is the one corresponding to formula (Ia) above in which R and R' both independently represent a hydrophobic group, X and X' each represent a group L", n and p are 0, and L, L', L" Y and m have the meaning given above. The fact that n and p are 0 means that these polymers do not comprise units derived from a monomer containing an amine function, incorporated into the polymer during the polycondensation. The protonated amine functions of these polyurethanes result from the hydrolysis of excess isocyanate functions, at the chain end, followed by alkylation of the primary amine functions formed with alkylating agents containing a hydrophobic group, i.e. compounds of the type RQ or R'Q, in which R and R' are as defined above and Q denotes a leaving group such as a halide, a sulfate, etc.

Yet another preferred family of cationic associative polyurethanes is the one corresponding to formula (Ia) above in which R and R' both independently represent a hydrophobic group, X and X' both independently represent a group comprising a quaternary amine, n and p are zero, and L, L', Y and m have the meaning given above.

When X and/or X' denote(s) a group comprising a tertiary or quaternary amine, X and/or X' may represent one of the following formulae:

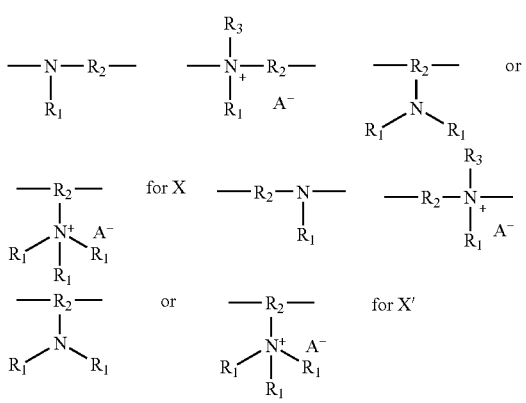

in which:

$R_2$ represents a linear or branched alkylene radical containing from 1 to 20 carbon atoms, optionally comprising a saturated or unsaturated ring, or an arylene radical, one or more of the carbon atoms possibly being replaced with a hetero atom chosen from N, S, O and P;

$R_1$ and $R_3$, which may be identical or different, denote a linear or branched $C_1$-$C_{30}$ alkyl or alkenyl radical or an aryl radical, at least one of the carbon atoms possibly being replaced with a hetero atom chosen from N, S, O and P;

$A^-$ is a physiologically acceptable counterion.

The groups L, L' and L" represent a group of formula:

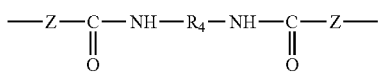

in which:

Z represents —O—, —S— or —NH—; and $R_4$ represents a linear or branched alkylene radical containing from 1 to 20 carbon atoms, optionally comprising a saturated or unsaturated ring, or an arylene radical, one or more of the carbon atoms possibly being replaced with a hetero atom chosen from N, S, O and P.

The groups P and P' comprising an amine function may represent at least one of the following formulae:

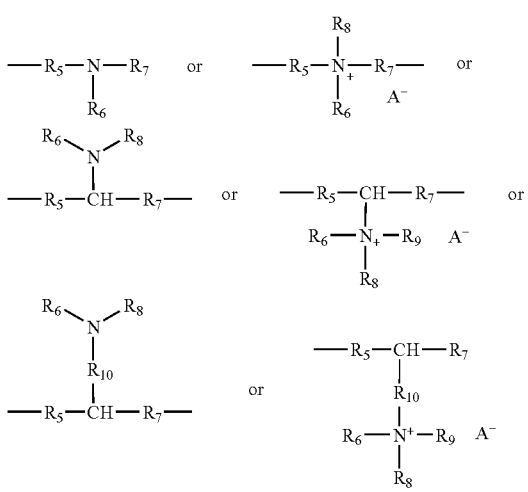

in which:

$R_5$ and $R_7$ have the same meanings as $R_2$ defined above;

$R_6$, $R_8$ and $R_9$ have the same meanings as $R_1$ and $R_3$ defined above;

$R_{10}$ represents a linear or branched, optionally unsaturated alkylene group possibly containing one or more hetero atoms chosen from N, O, S and P; and $A^-$ is a physiologically acceptable counterion.

As regards the meaning of Y, the term "hydrophilic group" means a polymeric or nonpolymeric water-soluble group.

By way of example, when it is not a polymer, mention may be made of ethylene glycol, diethylene glycol and propylene glycol.

When it is a hydrophilic polymer, in accordance with one preferred embodiment, mention may be made, for example, of polyethers, sulfonated polyesters, sulfonated polyamides or a mixture of these polymers. The hydrophilic compound is preferentially a polyether and in particular a poly(ethylene oxide) or poly(propylene oxide).

The cationic associative polyurethanes of formula (Ia) are formed from diisocyanates and from various compounds with functions containing a labile hydrogen. The functions containing a labile hydrogen may be alcohol, primary or secondary amine or thiol functions, giving, after reaction with the diisocyanate functions, polyurethanes, polyureas and polythioureas, respectively. The term "polyurethanes" encompasses these three types of polymer, namely polyurethanes per se, polyureas and polythioureas, and also copolymers thereof.

The hydrophobic group of the polyurethane of formula (Ia) may also result from the quaternization reaction of the tertiary amine of the compound comprising at least one tertiary amine unit. Thus, the hydrophobic group is introduced via the quaternizing agent. This quaternizing agent is a compound of the type RQ or R'Q, in which R and R' are as defined above and Q denotes a leaving group such as a halide, a sulfate, etc.

The hydrophilic group termed Y in formula (Ia) is optional. Specifically, the units containing a quaternary amine or protonated function may suffice to provide the solubility or water-dispersibility required for this type of polymer in an aqueous solution. Although the presence of a hydrophilic group Y is optional, cationic associative polyurethanes comprising such a group are, however, preferred.

(II) quaternized cellulose derivatives and polyacrylates containing non-cyclic amine side groups.

The quaternized cellulose derivatives are, in particular:
quaternized celluloses modified with groups comprising at least one fatty chain, such as alkyl, arylalkyl or alkylaryl groups comprising at least 8 carbon atoms, or mixtures thereof,
quaternized hydroxyethylcelluloses modified with groups comprising at least one fatty chain, such as alkyl, arylalkyl or alkylaryl groups comprising at least 8 carbon atoms, or mixtures thereof.

The alkyl radicals borne by the above quaternized celluloses or hydroxyethylcelluloses preferably comprise from 8 to 30 carbon atoms. The aryl radicals preferably denote phenyl, benzyl, naphthyl or anthryl groups.

Examples of quaternized alkylhydroxyethylcelluloses containing $C_8$-$C_{30}$ fatty chains that may be mentioned include the products Quatrisoft LM 200®, Quatrisoft LM-X 529-18-A®, Quatrisoft LM-X 529-18B® ($C_{12}$ alkyl) and Quatrisoft LM-X 529-8® ($C_{18}$ alkyl) sold by the company Amerchol, and the products Crodacel QM®, Crodacel QL® ($C_{12}$ alkyl) and Crodacel QS® ($C_{18}$ alkyl) sold by the company Croda.

(III) Cationic polyvinyllactams described by the Applicant in its patent application FR 01/01106. The said polymers comprise:
a) at least one monomer of vinyllactam or alkylvinyllactam type;
b) at least one monomer of structure (I) or (II) below:

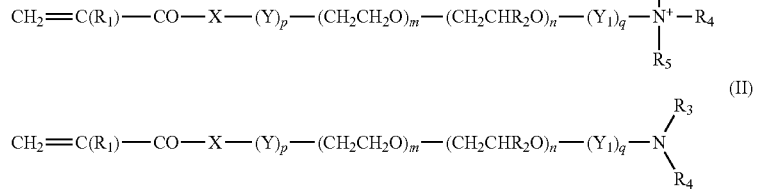

in which:
X denotes an oxygen atom or a radical $NR_6$,
$R_1$ and $R_6$ denote, independently of each other, a hydrogen atom or a linear or branched $C_1$-$C_5$ alkyl radical,
$R_2$ denotes a linear or branched $C_1$-$C_4$ alkyl radical,
$R_3$, $R_4$ and $R_5$ denote, independently of each other, a hydrogen atom, a linear or branched $C_1$-$C_{30}$ alkyl radical or a radical of formula (III):

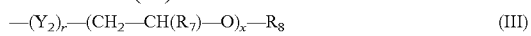

Y, $Y_1$ and $Y_2$ denote, independently of each other, a linear or branched $C_2$-$C_{16}$ alkylene radical,
$R_7$ denotes a hydrogen atom, a linear or branched $C_1$-$C_4$ alkyl radical, or a linear or branched $C_1$-$C_4$ hydroxyalkyl radical,
$R_8$ denotes a hydrogen atom or a linear or branched $C_1$-$C_{30}$ alkyl radical,
p, q and r denote, independently of each other, either the value 0 or the value 1,
m and n denote, independently of each other, an integer ranging from 0 to 100,
x denotes an integer ranging from 1 to 100,
Z denotes an organic or mineral acid anion,
with the proviso that:
at least one of the substituents $R_3$, $R_4$, $R_5$ or $R_8$ denotes a linear or branched $C_9$-$C_{30}$ alkyl radical,
if m or n is other than zero, then q is equal to 1,
if m or n is equal to zero, then p or q is equal to 0.

These cationic poly(vinyllactam) polymers may be crosslinked or non-crosslinked, random or block polymers. Preferably, $R_3$, $R_4$ and $R_5$ denote, independently of each other, a hydrogen atom or a linear or branched $C_1$-$C_{30}$ alkyl radical. More preferably, the monomer b) is a monomer of formula (I) for which m and n are equal to zero.

The vinyllactam or alkylvinyllactam is preferably a compound of structure (IV):

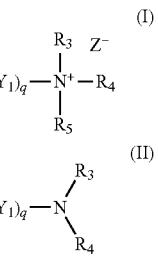

in which:
s denotes an integer ranging from 3 to 6,
$R_9$ denotes a hydrogen atom or a $C_1$-$C_5$ alkyl radical,
$R_{10}$ denotes a hydrogen atom or a $C_1$-$C_5$ alkyl radical,
with the proviso that at least one of the radicals $R_9$ and $R_{10}$ denotes a hydrogen atom.

Even more preferably, the monomer (IV) is vinylpyrrolidone.

The associative cationic poly(vinyllactam)s above may also contain one or more additional monomers, preferably cationic or nonionic monomers.

Cationic associative polymers that may especially be mentioned include the following terpolymers comprising at least:
a) one monomer of formula (IV),
b) one monomer of formula (I) in which p=1, q=0, $R_3$ and $R_4$ denote, independently of each other, a hydrogen atom or a $C_1$-$C_5$ alkyl radical and $R_5$ denotes a $C_9$-$C_{24}$ alkyl radical, and
c) a monomer of formula (II) in which $R_3$ and $R_4$ denote, independently of each other, a hydrogen atom or a $C_1$-$C_5$ alkyl radical.

Even more preferably, terpolymers comprising, by weight, 40% to 95% of monomer (a), 0.1% to 55% of monomer (c) and 0.25% to 50% of monomer (b) will be used.

Such polymers are described in patent application WO-00/68282.

As cationic poly(vinyllactam) polymers according to the invention, vinylpyrrolidone/dimethylaminopropylmethacrylamide/dodecyldimethylmethacrylamidopropylammonium tosylate terpolymers, vinylpyrrolidone/dimethylaminopropylmethacrylamide/cocoyldimethylmethacrylamidopropylammonium tosylate terpolymers, vinylpyrrolidone/dimethylaminopropylmethacrylamide/lauryldimethylmethacrylamidopropylammonium tosylate or chloride terpolymers are used in particular.

The amphoteric associative polymers are preferably chosen from those comprising least one non-cyclic cationic unit. Those comprising from 1 to 20 mol % of fatty-chain monomer are preferred.

The amphoteric associative polymers that are preferred according to the invention comprise or are prepared by copolymerizing:
1) at least one monomer of formula (Ia) or (Ib):

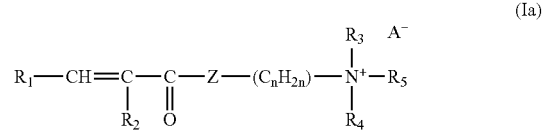

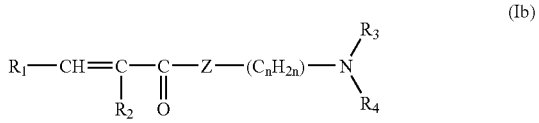

$$R_1—CH{=}C—\underset{\underset{O}{\|}}{C}—Z—(C_nH_{2n})—N\underset{R_4}{\overset{R_3}{\diagup}} \quad \text{(Ib)}$$
$$\phantom{R_1—CH{=}}\underset{R_2}{|}$$

in which $R_1$ and $R_2$, which may be identical or different, represent a hydrogen atom or a methyl radical, $R_3$, $R_4$ and $R_5$, which may be identical or different, represent a linear or branched alkyl radical containing from 1 to 30 carbon atoms, Z represents an NH group or an oxygen atom, n is an integer from 2 to 5, $A^-$ is an anion derived from an organic or mineral acid, such as a methosulfate anion or a halide such as chloride or bromide;

2) at least one monomer of formula (II):

$$R_6—CH{=}CR_7—COOH \quad \text{(II)}$$

in which $R_6$ and $R_7$, which may be identical or different, represent a hydrogen atom or a methyl radical; and 3) at least one monomer of formula (III):

$$R_6—CH{=}CR_7—COXR_8 \quad \text{(III)}$$

in which $R_6$ and $R_7$, which may be identical or different, represent a hydrogen atom or a methyl radical, X denotes an oxygen or nitrogen atom and $R_8$ denotes a linear or branched alkyl radical containing from 1 to 30 carbon atoms;

at least one of the monomers of formula (Ia), (Ib) or (III) comprising at least one fatty chain.

The monomers of formulae (Ia) and (Ib) are preferably chosen from the group formed by dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropylmethacrylamide, dimethylaminopropylacrylamide, these monomers optionally being quaternized, for example with a $C_1$-$C_4$ alkyl halide or a $C_1$-$C_4$ dialkyl sulfate.

More particularly, the monomer of formula (Ia) is chosen from acrylamidopropyltrimethylammonium chloride and methacrylamidopropyltrimethylammonium chloride.

The monomers of formula (II) are preferably chosen from the group consisting of acrylic acid, methacrylic acid, crotonic acid and 2-methylcrotonic acid. More particularly, the monomer of formula (II) is acrylic acid.

The monomers of formula (III) are preferably chosen from the group consisting of $C_{12}$-$C_{22}$ and more particularly $C_{16}$-$C_{18}$ alkyl acrylates or methacrylates.

In the amphoteric associative polymers, the ratio of the number of cationic charges/anionic charges is preferably equal to about 1.

These amphoteric associative polymers and the preparation thereof are described, for example, in patent application WO 98/44012.

Among these amphoteric associative polymers, acrylic acid/(meth)acrylamidopropyltrimethylammonium chloride/stearyl methacrylate terpolymers are preferred.

Finally, the nonionic associative polymers used in the present invention are preferably chosen from:

(1) celluloses, in particular hydroxyethylcelluloses, modified with groups comprising at least one fatty chain. Examples that may be mentioned include:

hydroxyethylcelluloses modified with groups comprising at least one fatty chain, such as alkyl, arylalkyl or alkylaryl groups, or mixtures thereof, and in which the alkyl groups are preferably $C_8$-$C_{22}$, for instance the product Natrosol Plus Grade 330 CS® ($C_{16}$ alkyl) sold by the company Aqualon, or the product Bermocoll EHM 100 sold by the company Berol Nobel, hydroxyethylcelluloses modified with alkylphenyl polyalkylene glycol ether groups, such as the product Amercell Polymer HM-1500® (nonylphenyl polyethylene glycol (15) ether) sold by the company Amerchol.

(2) hydroxypropyl guars modified with groups comprising at least one fatty chain, such as the product Esaflor HM 22® ($C_{22}$ alkyl chain) sold by the company Lamberti, and the products RE210-18® ($C_{14}$ alkyl chain) and RE205-1® ($C_{20}$ alkyl chain) sold by the company Rhône-Poulenc.

(3) copolymers of vinylpyrrolidone and of fatty-chain hydrophobic monomers; examples thereof that may be mentioned include:

the products Antaron V216® or Ganex V216® (vinylpyrrolidone/hexadecene copolymer) sold by the company ISP.

the products Antaron V220® or Ganex V220® (vinylpyrrolidone/eicosene copolymer) sold by the company ISP.

(4) copolymers of $C_1$-$C_6$ alkyl methacrylates or acrylates and of amphiphilic monomers comprising at least one fatty chain, such as, for example, the oxyethylenated methyl acrylate/stearyl acrylate copolymer sold by the company Goldschmidt under the name Antil 208®.

(5) copolymers of hydrophilic methacrylates or acrylates and of hydrophobic monomers comprising at least one fatty chain, such as, for example, the polyethylene glycol methacrylate/lauryl methacrylate copolymer.

(6) polyurethane polyethers comprising in their chain both hydrophilic blocks usually of polyoxyethylenated nature and hydrophobic blocks, which may be aliphatic sequences alone and/or cycloaliphatic and/or aromatic sequences.

Preferably, the polyurethane polyethers comprise at least two hydrocarbon-based lipophilic chains containing from 6 to 30 carbon atoms, separated by a hydrophilic block, the hydrocarbon-based chains possibly being pendent chains, or chains at the end of the hydrophilic block. In particular, it is possible for one or more pendent chains to be included. In addition, the polymer may comprise a hydrocarbon-based chain at one end or at both ends of a hydrophilic block.

The polyurethane polyethers may be multiblock, in particular in triblock form. Hydrophobic blocks may be at each end of the chain (for example: triblock copolymer with a hydrophilic central block) or distributed both at the ends and in the chain (for example: multiblock copolymer). These same polymers may also be graft polymers or starburst polymers.

The nonionic fatty-chain polyurethane polyethers may be triblock copolymers in which the hydrophilic block is a polyoxyethylenated chain comprising from 50 to 1000 oxyethylene groups. The nonionic polyurethane polyethers comprise a urethane linkage between the hydrophilic blocks, whence arises the name.

By extension, also included among the nonionic fatty-chain polyurethane polyethers are those in which the hydrophilic blocks are linked to the lipophilic blocks via other chemical bonds.

As examples of nonionic fatty-chain polyurethane polyethers that may be used in the invention, it is also possible to use Rheolate 205® containing a urea function, sold by the company Rheox, or Rheolate® 208, 204 or 212, and also Acrysol RM 184®.

Mention may also be made of the product Elfacos T210® containing a $C_{12-14}$ alkyl chain, and the product Elfacos T212® containing a $C_{18}$ alkyl chain, from Akzo.

The product DW 1206B® from Rohm & Haas containing a $C_{20}$ alkyl chain and a urethane linkage, sold at a solids content of 20% in water, may also be used.

It is also possible to use solutions or dispersions of these polymers, especially in water or in aqueous-alcoholic medium. Examples of such polymers that may be mentioned are Rheolate® 255, Rheolate® 278 and Rheolate® 244 sold by the company Rheox. The products DW 1206F and DW 1206J sold by the company Rohm & Haas may also be used.

The polyurethane polyethers that may be used according to the invention are in particular those described in the article by G. Fonnum, J. Bakke and Fk. Hansen—Colloid Polym. Sci 271, 380.389 (1993).

Even more particularly, according to the invention, it is preferred to use a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold especially by the company Rohm & Haas under the names Aculyn 46® and Aculyn 44®. Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%). Aculyn 44® is a polycondensate of polyethylene glycol containing 150 or 180 mol of ethylene oxide, of decyl alcohol and of methylenebis(4-cyclohexyl-isocyanate) (SMDI), at 35% by weight in a mixture of propylene glycol (39%) and water (26%).

(7) copolymers of PEG-180, of tetramethoxymethylglycouril and of laureth-50 or of octoxynol-40 (INCI names), sold under the names Pure Thix® 1450 and Pure Thixo 1451 by the company Sud-Chemie.

The associative polymers preferably used in the photoprotective compositions of the present invention are anionic associative polymers of family (IV), i.e. acrylic terpolymers of an α,β-unsaturated carboxylic acid, of a non-surfactant α,β-unsaturated monomer and of a surfactant monomer obtained by reacting an ethylenically unsaturated monoisocyanate and a monohydric surfactant, and in particular the product sold by the company Amerchol under the name Viscophobe DB 1000®.

The photoprotective system used in the photoprotective compositions of the present invention comprises:
  at least one metal oxide-based mineral nanopigment, and preferably, also at least one organic UV-A and/or UV-B screening agent.

The organic UV-A and/or UV-B screening agents that may be used may be chosen especially from cinnamic derivatives, dibenzoylmethane derivatives, salicylic derivatives, benzylidenecamphor derivatives, triazine derivatives such as those described in patents or patent applications U.S. Pat. No. 4,367,390, EP 0 863 145, EP 0 517 104, EP 0 570 838, EP 0 796 851, EP 0 775 698, EP 0 878 469, EP 0 933 376, EP 0 507 691, EP 0 507 692, EP 0 790 243, EP 0 944 624 and U.S. Pat. No. 4,724,137; benzophenone derivatives; β,β'-diphenylacrylate derivatives; benzotriazole derivatives, benzalmalonate derivatives, 4,4-diarylbutadienes, bis-benzoxazolyl derivatives as described in patents EP 669 323 and U.S. Pat. No. 2,463,264, methylenebis(hydroxyphenyl)benzotriazole derivatives as described in patent applications U.S. Pat. No. 5,237,071, U.S. Pat. No. 5,166,355, GB 2 303 549, DE 197 26 184 and EP 893 119, phenylbenzimidazole derivatives; anthranilic derivatives, imidazoline derivatives; p-aminobenzoic acid derivatives, screening hydrocarbon-based polymers and screening silicones such as those described especially in patent application WO 93/04665; dimers derived from α-alkylstyrene as described in patent application DE 198 55 649; and also mixtures of these screening agents.

As examples of such screening agents that are active in the UV-A and/or UV-B range, mention may be made of the following compounds, denoted by their INCI name, and also mixtures thereof:

Para-Aminobenzoic Acid Derivatives:
  PABA,
  Ethyl PABA,
  Ethyl dihydroxypropyl PABA,
  Ethylhexyl dimethyl PABA sold in particular under the trade name Escalol 507 by ISP,
  Glyceryl PABA,
  PEG-25 PABA sold under the trade name Uvinul P25 by BASF.

Salicylic Derivatives:
  Homosalate sold under the trade name Eusolex HMS by Rona/EM Industries,
  Ethylhexyl salicylate sold under the trade name Neo Heliopan OS by Haarmann and Reimer,
  Dipropylene glycol salicylate sold under the trade name Dipsal by Scher,
  TEA salicylate sold under the trade name Neo Heliopan TS by Haarmann and Reimer.

Dibenzoylmethane Derivatives:
  Butyl methoxydibenzoylmethane sold in particular under the trade name Parsol 1789 by Hoffmann LaRoche,
  Isopropyldibenzoylmethane.

Cinnamic Derivatives:
  Ethylhexyl methoxycinnamate sold in particular under the trade name Parsol MCX by Hoffmann LaRoche,
  Isopropyl methoxycinnamate,
  Isoamyl methoxycinnamate sold under the trade name Neo Heliopan E 1000 by Haarmann and Reimer,
  Cinoxate,
  DEA methoxycinnamate,
  Diisopropyl methylcinnamate,
  Glyceryl ethylhexanoate dimethoxycinnamate.

β,β-Diphenyl Acrylate Derivatives:
  Octocrylene sold in particular under the trade name Uvinul-539 by BASF,
  Etocrylene sold in particular under the trade name Uvinul N35 by BASF.

Benzophenone Derivatives:
  Benzophenone-1 sold under the trade name Uvinul 400 by BASF,
  Benzophenone-2 sold under the trade name Uvinul D-50 by BASF,
  Benzophenone-3 or Oxybenzone sold under the trade name Uvinul M-40 by BASF,
  Benzophenone-4 sold under the trade name Uvinul MS-40 by BASF,
  Benzophenone-5,
  Benzophenone-6 sold under the trade name Helisorb 11 by Norquay,
  Benzophenone-8 sold under the trade name Spectra-Sorb UV-24 by American Cyanamid,
  Benzophenone-9 sold under the trade name Uvinul DS-49 by BASF,
  Benzophenone-12,
  n-hexyl 2-(4-diethylamino-2-hydroxybenzoyl)benzoate.

Benzylidenecamphor Derivatives:
3-Benzylidenecamphor manufactured under the name Mexoryl SD by Chimex,
4-Methylbenzylidenecamphor sold under the name Eusolex 6300 by Merck, Benzylidenecamphorsulfonic acid manufactured under the name Mexoryl SL by Chimex,
   Camphor benzalkonium methosulfate manufactured under the name Mexoryl SO by Chimex,
   Terephthalylidenedicamphorsulfonic acid manufactured under the name Mexoryl SX by Chimex,
   Polyacrylamidomethylbenzylidenecamphor manufactured under the name Mexoryl SW by Chimex.
Phenylbenzimidazole Derivatives:
   Phenylbenzimidazolesulfonic acid sold in particular under the trade name Eusolex 232 by Merck,
   Benzimidazilate sold under the trade name Neo Heliopan AP by Haarmann and Reimer,
   Disodium phenyldibenzimidazoletetrasulfonate sold under the trade name Neo Heliopan AP by Haarmann and Reimer.
Triazine Derivatives:
   Anisotriazine sold under the trade name Tinosorb S by Ciba Geigy,
   Ethylhexyltriazone sold in particular under the trade name Uvinul T150 by BASF,
   Diethylhexylbutamidotriazone sold under the trade name Uvasorb HEB by Sigma 3V,
   2,4,6-Tris(diisobutyl 4'-aminobenzalmalonate) s-triazine.
Benzotriazole Derivatives:
   Drometrizole trisiloxane sold under the trade name Silatrizole by Rhodia Chimie,
   Methylenebis(benzotriazolyl)tetramethylbutylphenol sold in solid form under the trade name MIXXIM BB/100 by Fairmount Chemical, or in micronized form as an aqueous dispersion under the trade name Tinosorb M by Ciba Specialty Chemicals.
Anthranilic Derivatives:
   Menthyl anthranilate sold under the trade name Neo Heliopan MA by Haarmann and Reimer.
Imidazoline Derivatives:
   Ethylhexyldimethoxybenzylidenedioxoimidazoline propionate.
Benzalmalonate Derivatives:
   Polyorganosiloxanes, containing benzalmalonate functions, such as polysilicone-15, sold under the trade name Parsol SLX by Hoffmann LaRoche,
4,4-Diarylbutadienes:
   1,1-Dicarboxy(2,2'-dimethylpropyl)-4,4-diphenyl-butadiene.

The organic UV-screening agents that are more particularly preferred are chosen from the following compounds (INCI names):
   Ethylhexyl salicylate,
   Ethylhexyl methoxycinnamate,
   Octocrylene,
   Butyl methoxydibenzoylmethane,
   Phenylbenzimidazolesulfonic acid,
   Terephthalylidenedicamphorsulfonic acid,
   Benzophenone-3,
   Benzophenone-4,
   Benzophenone-5,
   n-Hexyl 2-(4-diethylamino-2-hydroxybenzoyl)benzoate,
   4-Methylbenzylidenecamphor,
   Terephthalylidenedicamphorsulfonic acid,
   Disodium phenyldibenzimidazoletetrasulfonate,
   2,4,6-Tris(diisobutyl 4'-aminobenzalmalonate)-s-triazine,
   Anisotriazine,
   Ethylhexyltriazone,
   Diethylhexylbutamidotriazone,
   Methylenebis(benzotriazolyl)tetramethylbutylphenol,
   Drometrizole trisiloxane,
   Polysilicone-15,
   1,1-Dicarboxy(2,2'-dimethylpropyl)-4,4-diphenylbutadiene,
   and mixtures thereof.

The metal oxide-based mineral nanopigments used in the present invention are powders consisting of particles with a mean elemental size generally of between 5 nm and 100 nm and preferably between 10 and 50 nm. The metal oxides forming these nanopigments may be chosen especially from titanium oxide, iron oxide, zinc oxide, zirconium oxide and cerium oxide. Titanium oxide, amorphous or in crystalline form (rutile and/or anatase), is most particularly preferred among these oxides. These nanopigments may be coated with a coating consisting, for example, of alumina and/or aluminium stearate, or a silane or silicone polymer.

These nanopigments and their use as photoprotective agents are known and described, for example, in patent applications EP 518 772 and EP 518 773.

Needless to say, the concentration of nanopigments and of organic UV-screening agents depends on the desired protection factor. It is generally between 0.5% and 10% by weight for the nanopigments, and between 0.1% and 30% and preferably between 0.5% and 15% for the organic UV-screening agents, all these concentrations being relative to the total weight of the photoprotective composition.

The nature of the fatty phase serving to prepare the photoprotective emulsions according to the invention is not critical, and it may thus consist of any known compound suitable for the manufacture of oil-in-water emulsions. In particular, these compounds may be chosen from various fatty substances, oils of plant, animal or mineral origin, natural or synthetic waxes, and the like.

Among the oils that can form part of the composition of the fatty phase, mention may be made especially of:
   mineral oils such as liquid paraffin and liquid petroleum jelly,
   oils of animal origin such as perhydrosqualene,
   oils of plant origin such as sweet almond oil, avocado oil, castor oil, olive oil, jojoba oil, sesame seed oil, groundnut oil, grapeseed oil, rapeseed oil, coconut oil, hazelnut oil, shea butter, palm oil, apricot kernel oil, beauty-leaf oil, rice bran oil, maize germ oil, wheatgerm oil, soybean oil, sunflower oil, evening primrose oil, safflower oil, passionflower oil and rye oil,
   synthetic oils such as purcellin oil, butyl myristate, isopropyl myristate, cetyl myristate, isopropyl palmitate, isopropyl adipate, ethylhexyl adipate, butyl stearate, hexadecyl stearate, isopropyl stearate, octyl stearate, isocetyl stearate, decyl oleate, hexyl laurate, propylene glycol dicaprylate and esters derived from lanolic acid, such as isopropyl lanolate and isocetyl lanolate, isoparaffins and poly-α-olefins.

As other oils that may be used in the emulsions according to the invention, mention may also be made of $C_{12}$-$C_{15}$ fatty alkyl benzoates (Finsolv TN from Finetex), fatty alcohols such as lauryl alcohol, cetyl alcohol, myristyl alcohol, stearyl alcohol, palmityl alcohol, oleyl alcohol and 2-octyldodecanol, acetyl glycerides, octanoates and decanoates of alcohols and of polyalcohols, such as those of glycol and of glycerol, ricinoleates of alcohols and of polyalcohols such as cetyl ricinoleate, fatty acid triglycerides such as caprylic/capric triglycerides, triglycerides of $C_{10}$-$C_{18}$ saturated fatty acids, fluoro oils, perfluoro oils, lanolin, hydrogenated lanolin, acetylated lanolin and, finally, volatile or non-volatile silicone oils.

The oily phase of the emulsion preferably represents from 0.1% to 45% and in particular from 5% to 30% of the total weight of the liquid phase.

Needless to say, the fatty phase may also contain one or more standard lipophilic cosmetic adjuvants, especially those that are already usually used in the manufacture and production of antisun cosmetic compositions.

The continuous aqueous phase may conventionally consist of water or a mixture of water and polyhydric alcohol(s), for instance glycerol, propylene glycol and sorbitol, or alternatively a mixture of water and of water-soluble lower alcohol(s) such as ethanol, isopropanol or butanol, and it can, of course, also contain standard water-soluble cosmetic adjuvants.

The photoprotective compositions according to the invention may also contain agents for artificially tanning and/or browning the skin (self-tanning agents). The self-tanning agents are generally chosen from monocarbonyl or polycarbonyl compounds, for instance isatin, alloxan, ninhydrin, glyceraldehyde, mesotartaric aldehyde, glutaraldehyde, erythrulose, pyrazoline-4,5-dione derivatives as described in patent application FR 2 466 492 and WO 97/35842, dihydroxyacetone (DHA) and 4,4-dihydroxypyrazolin-5-one derivatives as described in patent application EP 903 342. DHA will preferably be used. The DHA may be used in free form and/or in encapsulated form, for example in lipid vesicles such as liposomes, described especially in patent application WO 97/25970.

The monocarbonyl or polycarbonyl self-tanning agents when they are present are generally used in proportions ranging from 0.1% to 10% by weight relative to the total weight of the composition and preferably from 0.2% to 8% by weight relative to the total weight of the composition.

The compositions of the present invention may also comprise standard cosmetic adjuvants chosen especially from thickeners and/or gelling agents, softeners, humectants, opacifiers, stabilizers, emollients, silicones, insect repellents, fragrances, preserving agents, fillers, pigments, propellants, acidifying or basifying agents or any other ingredient usually used in cosmetics and/or dermatology.

Needless to say, a person skilled in the art will take care to select the optional additional compound(s) mentioned above and/or the amounts thereof such that the advantageous properties intrinsically associated with the emulsions in accordance with the invention are not, or are not substantially, adversely affected by the envisaged addition(s).

A subject of the invention is also a process for preparing such emulsified photoprotective compositions, comprising the homogenization, at a temperature of between 40 and 70° C. and using a mixer or a homogenizer of rotor-stator type, of a fatty phase optionally containing a gemini surfactant, optionally one or more organic UV-screening agents, and optionally one or more nanopigment(s), and of an aqueous phase optionally containing a gemini surfactant, optionally one or more organic UV-screening agents and optionally one or more nanopigment(s), it being understood that at least one of these phases contains a gemini surfactant, an associative polymer being incorporated either into the aqueous phase or into the fatty phase before homogenization, or into the fine emulsion obtained, after cooling to a temperature of between 30 and 40° C.

The nanopigment(s) may also be incorporated in pulverulent form into the oil-in-water emulsion containing the associative polymer. In this case, it is necessary to subject the composition to a second homogenization step.

The process of the present invention is distinguished by the fact that it may be performed without any high-pressure homogenization step.

EXAMPLE 1

|  | Concentration (% by weight) |
|---|---|
| Phase A | |
| Ceralution ® H | 2.5 |
| C12-15 alkyl benzoate | 11.15 |
| Isohexadecane | 5.6 |
| Octocrylene | 9 |
| Butylmethoxydibenzoylmethane | 2.5 |
| Drometrizole trisiloxane | 0.75 |
| Preserving agent | qs |
| Phase B | |
| Water | qs 100 |
| Disodium ethylenediaminetetramethylenephosphonate | 0.1 |
| Terephthalylidenedicamphorsulfonic acid | 0.75 |
| Cetylhydroxyethylcellulose (Natrosol Plus Grade 330CS sold by Aqualon) | 0.5 |
| Triethanolamine | 5 |
| Phase C | qs |
| Titanium dioxide | 5 |
| Phase D | |
| Preserving agent | |

Procedure for preparing a photoprotective composition according to the invention: Phases A and B are heated separately to a temperature of about 70° C. and these two combined phases are then subjected to homogenization using a rotor-stator machine. Titanium dioxide (phase C) in pulverulent form is added to the emulsion obtained and a second homogenization is performed. After cooling to 25° C., the preserving agent (Phase D) is added.

EXAMPLE 2

|  | Concentration (% by weight) |
|---|---|
| Phase A | |
| Ceralution ® H | 1 |
| Caprylic/capric triglyceride | 5 |
| Cyclopentasiloxane | 4 |
| C12-15 alkyl benzoate | 2.5 |
| Triethyl citrate | 4 |
| Isotrideceth-12 | 2 |
| Octocrylene | 9 |
| Butylmethoxydibenzoylmethane | 2.5 |
| Phase B | |
| Water | 6 |
| Ceralution ® F | 1.5 |
| Xanthan gum | 0.1 |
| Glycerol | 6 |
| Phase C | |
| Water | qs 100 |
| Vinylpyrrolidone/eicosene copolymer (Antaron V220 ® sold by the company ISP) | 1 |

-continued

| | Concentration (% by weight) |
|---|---|
| Denatured alcohol | 6 |
| Terephthalylidenedicamphorsulfonic acid | 0.75 |
| Triethanolamine | qs |
| Phase D | |
| Trimethoxycaprylylsilane-coated titanium dioxide | 5 |

Procedure for preparing a photoprotective composition according to the invention: Phases A and B are heated separately to a temperature of about 60° C., titanium dioxide (phase D) is added to phase A with stirring using a rotor-stator machine, the phase A+D mixture is poured into phase B, and the whole is then homogenized. The mixture obtained is allowed to cool to a temperature of about 40° C. and phase C is incorporated therein via a second homogenization step.

EXAMPLE 3

| | Concentration (% by weight) |
|---|---|
| Phase A | |
| Ceralution ® H | 1 |
| Caprylic/capric triglyceride | 5 |
| C12-15 alkyl benzoate | 6.5 |
| Dicaprylyl carbonate | 4 |
| Isotrideceth-12 | 2 |
| Octocrylene | 9 |
| Butylmethoxydibenzoylmethane | 2.5 |
| Phase B | |
| Water | 6 |
| Ceralution ® F | 1.5 |
| Glycerol | 6 |
| Phase C | |
| Water | qs 100 |
| PEG-150/stearyl alcohol/SMDI copolymer (15%)/Aqua (Aculyn 46 ® sold by Rohm & Haas) | 3 |
| Terephthalylidenedicamphorsulfonic acid | 0.75 |
| Triethanolamine | qs |
| Phase D | |
| Titanium dioxide coated with aluminium hydroxide and stearic acid | 5 |
| Phase E | |
| Phenoxyethanol and methylparaben and ethylparaben and butylparaben and isobutylparaben and propylparaben | 1 |

Procedure for preparing a photoprotective composition according to the invention: Phases A and B are heated separately to a temperature of about 60° C., phase D is incorporated into the heated phase A with stirring using a rotor-stator machine, and the phase A+D mixture is then poured into phase B. After homogenizing the mixture, it is allowed to cool to 40° C. and phase C is added. After a further homogenization step, the mixture is cooled to 25° C. and the preserving agent (phase E) is added.

EXAMPLE 4

| | Concentration (% by weight) |
|---|---|
| Phase A | |
| Ceralution ® H | 1 |
| C12-15 alkyl benzoate | 8 |
| Isohexadecane | 5 |
| Isotrideceth-12 | 0.5 |
| Octocrylene | 9 |
| Butylmethoxydibenzoylmethane | 2.5 |
| Drometrizole trisiloxane | 0.75 |
| Phenoxyethanol and methylparaben and ethylparaben and butylparaben and isobutylparaben and propylparaben | 1 |
| Phase B | |
| Water | 12 |
| Ceralution ® F | 1.5 |
| Pentasodium ethylenediaminetetramethylenephosphonate | 0.3 |
| Phenoxyethanol and methylparaben and ethylparaben and butylparaben and isobutylparaben and propylparaben | 0.25 |
| Terephthalylidenedicamphorsulfonic acid | 0.75 |
| Triethanolamine | qs |
| Phase C | |
| Titanium dioxide | 5 |
| Phase D | |
| Water | qs 100 |
| Polyacrylate-3 (25%)/Aqua (Viscophobe DB 1000 ® sold by the company Amerchol) | 0.5 |
| Triethanolamine | qs |

Procedure for preparing a photoprotective composition according to the present invention: Phases A and B are heated separately to a temperature of about 60° C., and the two phases are mixed together and stirred using a rotor-stator mixer. After addition of the titanium dioxide (phase C) in pulverulent form, the mixture is homogenized and allowed to cool to 40° C. Finally, phase D is added to the emulsion obtained and the whole is homogenized again.

The invention claimed is:

1. A photoprotective composition for protecting the skin and/or the hair against UV radiation, comprising:
    (1) as liquid phase, an oil-in-water emulsion, emulsified with at least one dimeric surfactant comprising two surfactant units, which are identical or different, each comprising a hydrophilic head and a hydrophobic tail and connected to each other, via the hydrophilic heads, by means of a spacer group, said dimeric surfactant being an anionic dimeric surfactant of formula (I):

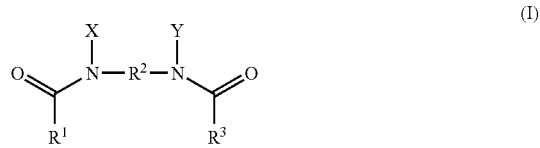

in which
- $R^1$ and $R^3$ are identical and each represent a linear $C_{8-16}$ alkyl group, $R^2$ represents a $C_{2-8}$ alkylene group, and X and Y each represent a group $(C_2H_4O)_x$—RF with x=10-15 and
- RF=—$SO_3M$, in which M represents an alkali metal ion, the concentration of the dimeric surfactant(s) being between 0.01% and 4% by weight relative to the total weight of the photoprotective composition;

(2) a photoprotective system which screens out UV rays, comprising at least one mineral nanopigment based on metal oxide, the concentration of the nanopigment(s) being between 0.5% and 10% by weight relative to the total weight of the photoprotective composition; and (3) at least one nonionic associative polymer comprising at least one $C_{8-40}$ fatty chain, which is a hydroxyethylcellulose modified with a group having at least one fatty chain or a polyether-polyurethane having hydrophilic blocks and at least one fatty chain, the concentration of the associative polymer(s) being between 0.01% and 10% by weight relative to the total weight of the photoprotective composition.

2. The photoprotective composition according to claim 1, wherein:
(a) the anionic dimeric surfactant is sodium dicocoylethylenediamine PEG-15 sulfate (INCI name) having the following formula:

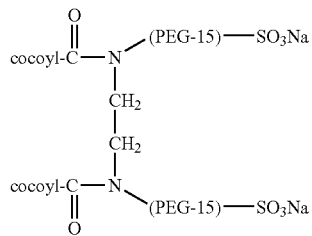

(b) the nonionic associative polymer is a hydroxyethylcellulose modified with alkyl, aralkyl or alkylaryl groups or mixtures thereof wherein the alkyl groups are $C_8$-$C_{22}$; or the nonionic associative polymer is a polyurethane polyether which is the polycondensate of (i) polyethylene glycol containing 150 or 180 mol of ethylene oxide; (ii) stearyl alcohol or decyl alcohol; and (iii) methylenebis (4-cyclohexylisocyanate) (SMDI).

3. The photoprotective composition according to claim 1, wherein the metal oxide-based nanopigment(s) is (are) selected from the group consisting of titanium oxide, iron oxide, zinc oxide, zirconium oxide and cerium oxide, which are optionally coated.

4. The photoprotective composition according to claim 3, wherein the metal oxide-based nanopigments are nanopigments based on amorphous or crystalline titanium dioxide.

5. The photoprotective composition according to claim 2, wherein the metal oxide-based nanopigment(s) is (are) selected from the group consisting of titanium oxide, iron oxide, zinc oxide, zirconium oxide and cerium oxide, which are optionally coated.

6. The photoprotective composition according to claim 5, wherein the metal oxide-based nanopigments are nanopigments based on amorphous or crystalline titanium dioxide.

7. The photoprotective composition according to claim 1, wherein the photoprotective system which screens out UV rays also comprises at least one organic UV-A and/or UV-B screening agent.

8. The photoprotective composition according to claim 7, wherein the organic UV-A and/or UV-B screening agent(s) is (are) selected from the group consisting of PABA, ethyl PABA, ethyl dihydroxypropyl PABA, ethylhexyl dimethyl PABA, glyceryl PABA, PEG-25 PABA, homosalate, ethylhexyl salicylate, dipropylene glycol salicylate, TEA salicylate, butyl methoxydibenzoylmethane, isopropyldibenzoylmethane, ethylhexyl methoxycinnamate, isopropyl methoxycinnamate, isoamyl methoxycinnamate, cinoxate, DEA methoxycinnamate, diisopropyl methylcinnamate, glyceryl ethylhexanoate dimethoxycinnamate, octocrylene, etocrylene, benzophenone-1, benzophenone-2, benzophenone-3, benzophenone-4, benzophenone-5, benzophenone-6, benzophenone-8, benzophenone-9, benzophenone-12, n-hexyl 2-(4-diethylamino-2-hydroxybenzoyl)benzoate, 3-benzylidenecamphor, 4-methylbenzylidenecamphor, benzylidenecamphorsulfonic acid, camphor benzalkonium methosulfate, terephthalylidenedicamphorsulfonic acid, polyacrylamidomethylbenzylidenecamphor, phenylbenzimidazolesulfonic acid, benzimidazilate, disodium phenyldibenzimidazoletetrasulfonate, anisotriazine, ethylhexyltriazone, diethylhexylbutamidotriazone, 2,4,6-tris(diisobutyl-4'-aminobenzolmalonate)-s-triazine, drometrizole trisiloxane, methylenebis(benzotriazolyl)tetramethylbutylphenol, menthyl anthranilate, ethylhexyldimethoxybenzylidenedioxoimidazoline propionate, polysilicone-15 and 1,1-dicarboxy-(2,2'-dimethylpropyl); 4,4-diphenylbutadiene, and mixtures of these screening agents.

9. The photoprotective composition according to claim 8, wherein the organic UV-A and/or UV-B screening agent(s) is (are) selected from the group consisting of butyl methoxydibenzoylmethane, isopropyldibenzoylmethane, octocrylene, etocrylene, 3-benzylidenecamphor, 4-methylbenzylidenecamphor, benzylidenecamphorsulfonic acid, camphor benzalkonium methosulfate, terephthalylidenedicamphorsulfonic acid, polyacrylamidomethylbenzylidenecamphor, drometrizole trisiloxane, and mixtures of these screening agents.

10. The photoprotective composition according to claim 7, wherein the concentration of UV-A and/or UV-B screening agents is between 0.1% and 30% by weight relative to the total weight of the photoprotective composition.

11. The photoprotective composition according to claim 9, wherein the organic UV-A and/or UV-B screening agent(s) is (are) selected from the group consisting of butyl methoxydibenzoylmethane, octocrylene, drometrizole trisiloxane and terephthalylidenedicamphorsulfonic acid, and mixtures thereof.

12. The photoprotective composition according to claim 2, wherein the photoprotective system which screens out UV rays also comprises at least one organic UV-A and/or UV-B screening agent.

13. The photoprotective composition according to claim 12, wherein the organic UV-A and/or UV-B screening agent(s) is (are) selected from the group consisting of PABA, ethyl PABA, ethyl dihydroxypropyl PABA, ethylhexyl dimethyl PABA, glyceryl PABA, PEG-25 PABA, homosalate, ethylhexyl salicylate, dipropylene glycol salicylate, TEA salicylate, butyl methoxydibenzoylmethane, isopropyldibenzoylmethane, ethylhexyl methoxycinnamate, isopropyl methoxycinnamate, isoamyl methoxycinnamate, cinoxate, DEA methoxycinnamate, diisopropyl methylcinnamate, glyceryl ethylhexanoate dimethoxycinnamate, octocrylene, etocrylene, benzophenone-1, benzophenone-2, benzophenone-3, benzophenone-4, benzophenone-5, benzophenone-6, benzophenone-8, benzophenone-9, benzophenone-12, n-hexyl 2-(4-diethylamino-2-hydroxybenzoyl)benzoate, 3-benzylidenecamphor, 4-methylbenzylidenecamphor, benzylidenecamphorsulfonic acid, camphor benzalkonium methosulfate, terephthalylidenedicamphorsulfonic acid, polyacrylamidomethylbenzylidenecamphor, phenylbenzimidazolesulfonic acid, benzimidazilate, disodium phenyldibenzimidazoletetrasulfonate, anisotriazine, ethylhexyltriazone, diethylhexylbutamidotriazone, 2,4,6-tris(diisobutyl-4'-aminobenzolmalonate)-s-triazine, drometrizole trisiloxane, methylenebis(benzotriazolyl)tetramethylbutylphenol, menthyl anthranilate, ethylhexyldimethoxybenzylidenedioxoimidazoline propionate, polysilicone-15 and 1,1-dicarboxy-(2,2'-dimethylpropyl); 4,4-diphenylbutadiene, and mixtures of these screening agents.

14. The photoprotective composition according to claim 13, wherein the organic UV-A and/or UV-B screening agent(s) is (are) selected from the group consisting of butyl methoxydibenzoylmethane, isopropyldibenzoylmethane, octocrylene, etocrylene, 3-benzylidenecamphor, 4-methylbenzylidenecamphor, benzylidenecamphorsulfonic acid, camphor benzalkonium methosulfate, terephthalylidenedicamphorsulfonic acid, polyacrylamidomethylbenzylidenecamphor, drometrizole trisiloxane, and mixtures of these screening agents.

15. The photoprotective composition according to claim 14, wherein the organic UV-A and/or UV-B screening agent(s) is (are) selected from the group consisting of butyl methoxydibenzoylmethane, octocrylene, drometrizole trisiloxane and terephthalylidenedicamphorsulfonic acid, and mixtures thereof.

16. The photoprotective composition according to claim 1, wherein the concentration of the dimeric surfactant is between 0.05% and 3% by weight relative to the total weight of the photoprotective composition.

17. The photoprotective composition according to claim 1, wherein the concentration of the associative polymer(s) is between 0.1% and 5% by weight relative to the total weight of the photoprotective composition.

18. The photoprotective composition according to claim 10, wherein the concentration of UV-A and/or UV-B screening agents is between 0.5 and 15% by weight relative to the total weight of the photoprotective composition.

19. The photoprotective composition according to claim 1, further comprising agents for artificially tanning and/or browning the skin.

20. The photoprotective composition according to claim 1, having a viscosity, measured at 25° C. using a Brookfield viscometer with a No. 7 needle, of less than 200 mPa·s.

21. The photoprotective composition according to claim 20, having a viscosity, measured at 25° C. using a Brookfield viscometer with a No. 7 needle, of between 10 and 180 MPa·s.

22. A process for preparing a photoprotective composition according to claim 1, comprising homogenizing, at a temperature of between 40 and 70° C. and using a mixer or a homogenizer of rotor-stator type, an oil phase optionally comprising:
   (a)(1) said at least one dimeric surfactant,
   (a)(2) one or more organic UV-screening agents, and
   (a)(3) said at least one mineral nanopigment; and
an aqueous phase optionally comprising:
   (b)(1) said at least one dimeric surfactant,
   (b)(2) one or more organic UV-screening agents, and
   (b)(3) said at least one mineral nanopigment;
wherein (1) at least one of the phases comprises one or more of said at least one dimeric surfactant, and (2) said at least one nonionic associative polymer is incorporated either into the aqueous phase or into the fatty phase before homogenization, or into a fine emulsion obtained, after homogenizing and cooling to a temperature of between 30 and 40° C.;
provided that when said at least one mineral nanopigment is not included in said oil phase or in said aqueous phase, then said at least one mineral nanopigment is incorporated in pulverulent form into the oil-in-water emulsion obtained after homogenization, via a second step of homogenizing of the composition.

* * * * *